US006387674B1

(12) United States Patent
Trasciatti et al.

(10) Patent No.: US 6,387,674 B1
(45) Date of Patent: May 14, 2002

(54) CATALYTIC MONOCLONAL ANTIBODIES WITH PROTEASE ACTIVITY FOR SELECTIVE LYSIS OF PROTEIN COMPONENT OF PLAQUES AGGREGATES PATHOLOGICAL CONDITIONS

(75) Inventors: Silvia Trasciatti; Sergio Rosini, both of Pisa (IT)

(73) Assignee: Abiogen Pharma S.p.A., Pisa (IT)

( * ) Notice: Subject to any disclaimer, the term of this patent is extended or adjusted under 35 U.S.C. 154(b) by 0 days.

(21) Appl. No.: 09/463,724
(22) PCT Filed: Jul. 28, 1998
(86) PCT No.: PCT/EP98/04706
  § 371 Date: Jan. 31, 2000
  § 102(e) Date: Jan. 31, 2000
(87) PCT Pub. No.: WO99/06066
  PCT Pub. Date: Feb. 11, 1999

(30) Foreign Application Priority Data

Jul. 30, 1997 (IT) .......................................... MI97A1826

(51) Int. Cl.[7] .................................................. C12N 9/00
(52) U.S. Cl. .................... 435/188.5; 435/346; 424/94.1; 530/324
(58) Field of Search ..................... 425/188.5; 424/94.1; 530/324; 435/346

(56) References Cited

U.S. PATENT DOCUMENTS 5,258,289 A  11/1993  Davis et al. ................ 435/96.6
5,318,897 A  * 6/1994  Paul .......................... 435/68.1

FOREIGN PATENT DOCUMENTS

WO   89/10754   11/1989
WO   97/03696   2/1997

OTHER PUBLICATIONS

Solomon, B., et al. (1997) Proc Natl. Acad. Sci., USA 94, 4109–4112.*
Paul, S. (1996) Mol. Biotech. 5, 197–207.*
Hanin et al, "Characterization of a monoclonal antibody produced . . . ," Journal of Immunological Methods, vol. 173, pp. 139–147 (1994).
Gravina et al, "Amyloid β Protein (Aβ) in Alzheimer's Disease Brain," J. Bio. Chem., vol. 270, No. 13, pp. 7013–7016 (1985).

* cited by examiner

Primary Examiner—Charles L. Patterson, Jr.
(74) Attorney, Agent, or Firm—Nixon & Vanderhye P.C.

(57) ABSTRACT

Catalytic monoclonal antibodies (abzymes) with selective protease activity in the pathologies characterized by the presence of plaques and fibrillar aggregates with protein component; methods for the preparation thereof and the use thereof as medicaments in the treatment of pathologies such as Alzheimer's disease, amyloidosis, atherosclerosis, prions diseases.

11 Claims, No Drawings

CATALYTIC MONOCLONAL ANTIBODIES WITH PROTEASE ACTIVITY FOR SELECTIVE LYSIS OF PROTEIN COMPONENT OF PLAQUES AGGREGATES PATHOLOGICAL CONDITIONS

The present invention relates to catalytic monoclonal antibodies, in particular with protease activity, for the selective lysis of the protein component of plaques and aggregates related to pathological conditions.

Alzheimer's Disease

Alzheimer's disease (AD) is a degenerative disease which affects central nervous system, mainly at the level of those areas related to the intellectual functions, causing necrosis of the neuronal cells and, as a consequence, the progressive loss of cognitive, mental and mnemonic abilities of the concerned patients with inevitably fatal outcome.

AD, which can be diagnosed definitely only by autopsy, is characterized by pathological structures which can be distinguished in:

senile or amyloid plaques, localized in the extracellular space, which deposit in the brain and in the walls of cerebral blood vessels;

neurofibrillar tangles localized inside the cells.

The formation of said structures causes a remarkable loss of neurons in neocortex, hippocampus and other related structures, with a great reduction of the neurotransmitter concentration. Said effects are due to the toxicity determined both directly and indirectly by the cited neuro-pathological structures and the neuron death results, in its turn, in the progressive loss of the cognitive capacities.

The anatomic-pathological structures cited above consist of specific components:

1—β-amyloid Peptide (Aβ, A4, A4β, β,β-peptide), which derives by the processing of the amyloid precursor protein (βAPP), and is a mixture of a small group of peptides, 28 to 43 amino acid long, arranged in planar sheet structures.
2—Apolipoprotein E (Apo E)
3—Protein tau.

Aβ peptide is the main component of amyloid plaques; at least two different forms of plaques exist, which are likely to represent two subsequent steps of the Aβ polymerization process:

a) diffused or preamyloid plaques, which consist of amorphous, non Congo-philic deposits of insoluble Aβ, with few amyloid depositions, containing few reactive astrocytes or microglia; these are usually localized in brain's gray matter and apparently do not cause remarkable effects on the adjacent tissues;

b) senile or neuritic plaques which consist of a core of fibrillar, Congo-philic deposits of Aβ, containing reactive astrocytes or microglia and surrounded by degenerative, dystrophic neurites Protein tau associated with microtubules, in the hyperphosphorylated form, is the major component of the neurofibrillar tangles. These are usually formed by paired helical filaments (PHF) which, in their turn, derive from microtubule associated: proteins (MAPs) and consist of an abnormal accumulation in the degenerative neurons with cytoskeletal proteins with specific biochemical and antigenic properties. Under normal conditions MAPs probably regulate movement and stabilize the arrangement of neurons during the growth of axons and of dendrites.

ApoE is present in combination with the amyloid plaques, with the neurofibrillar forms and with the amyloid deposits of cerebral vases. ApoE could play a biochemical role in the development of AD, related to its capability of binding Aβ. ApoE supposedly plays the role of molecular carrier and it could assist in sequestrating Aβ in the plaques.

Early AD genetic analysis revealed mutations of some genes on different chromosomes.

In correlation with the characteristic presence of Aβ, a mutation of the gene which codifies for βAPP has been identified on chromosome 21, at the levels of codons 717 and 670/671. A punctiform mutation at said levels can change the βAPP processing, preventing the physiological cleavage in non-aggregating peptides and favouring, on the contrary, the amyloidogenic pathway. It should, however, be noted that only a small percentage of early cases of familial AD (4–5%) has been related to mutations on chromosome 21.

A second mutation strictly related with familial, early AD, has been identified on the long arm of chromosome 14. On the involved gene, named S182, at least 15 different mutations were detected, related with familial AD, said mutations appearing in 80% of the early AD cases. The product of gene S182 is a membrane integral protein, whose function has not yet been clarified.

A third gene, whose mutation is related with about 15% of the cases of familial early AD, is localized on chromosome 1 and is named STM2. The function of the protein codified by said gene is not yet known, but it seems to cause an increase in the production of β amyloid.

As far as senile AD is concerned, this could be the result of oligogenic mutations. This has been observed to be related to mutations on chromosome 19, in particular against the gene encoding for ApoE.

βAPP is a transmembrane glycoprotein (695–770 aa) which for the most part protrudes in the extracellular space. The physiological processing of βAPP consists in the cleavage by the enzyme α-secretase within the Aβ sequence, immediately outside the transmembrane region (aa 16), with formation and release of (AAPs) amyloid soluble forms in the extracellular fluid. The action of α-secretase, therefore, prevents the formation of Aβ. The amino acid sequence of βAPP corresponding to Aβ is localized in part in the extracellular space and in part in the membrane (the 28 aa from the amino-terminal to the transmembrane single domain of the precursor, plus the first 11–15 residues of the transmembrane domain). The βAPP expression and APPs release are modulated by neurotrophic factors and by cytokines. The expression of βAPP increases when the neuronal differentiation takes place and APPs can affect the neurite growth and neuron survival in cell cultures. The function of βAPP is not clear: apparently it can play an adhesive/receptor role and be involved in synaptic plasticity. APPs control $[Ca^{2+}]_i$ and modify the $Ca^{2+}$ response to glutamate. APPs are transported along the axon and are then released in the synapses by the growing axon cones and by the axon terminals.

In short, the functions of βAPP and of APPs are:

regulation of cell proliferation in non-neuronal cells, cellular adhesion, promotion of neuron survival, protection from excito-toxycity or from ischemic damages, regulation of neuron growth, regulation of calcium intracellular levels.

When the degradation of βAPP does not take place physiologically, either due to the presence of the punctiform mutation or to the attack by enzymes different from α-secretase or to an excessive production of βAPP, amyloidogenic fragments form, i.e. insoluble fragments of Aβ, with a planar β-sheet structure, aggregate in more and more complex fibrous formations until insoluble extracellular amyloid plaques are formed (Cummings, Neuroscience 48:763 (1992); Kuo, Neurobiol. Aging 14:547–560 (1993)).

In the core of neuritic plaques, a prevalent Aβ form 42 amino acid long has been identified, namely $A\beta_{1-42}$ (Rohrer, Proc. Natl. Acad. Sci. 90:10836–10840 (1993); Gravina, J. Biol. Chem. 270: 7013–7016 (1995); Motter, Ann. Neurol. 38: 643–648 (1995); Cummings, Neurobiol. Aging. 17: 653–659 (1996). This fragment, besides being the major component of amyloid plaques, is, among the various fragments, the one with the highest amyloidogenic characteristics, i.e. it is highly capable of associating in more and more complex aggregates and of forming fibrils. A more hydrophobic domain has, in fact, been evidenced on the $A\beta_{1-42}$ molecule which seems to be critical for the assemblage of amyloid fibrils, in that it increases the aggregation rate thereof (Pike, J. Neuroscience 13:1676 (1993); $A\beta_{1-42}$ could therefore play a more important role than the shorter fragments in the formation of plaques. Following the formation of the first fibrillar aggregates consisting of $A\beta_{1-42}$, other shorter fragments also aggregate in the plaques; $A\beta_{1-42}$ would therefore serve as a nucleation core for the aggregation.

$A\beta_{1-42}$ is deposited early and selectively in the senile plaques and this is a steady characteristic of all of the AD forms. $A\beta_{1-42}$ aggregates in fibrils and, already at this stage, i.e. before the fibrils are deposited in the amyloid plaques, the fibrils themselves can start the neurodegenerative process and also induce hyperphosphorylation of protein tau. The C-terminal amino acid is apparently critical for the aggregation of the peptide (Jarrett, Biochemistry 32:4693–4697 (1993).

A direct relationship exists between peptide aggregation and neurotoxic potentiality. Aβ has, in fact, a direct toxic effect on in vitro human neurons and such toxicity is directly proportional to the aggregation state. Aβ accumulates in or on the plasmatic membrane (it is incorporated in the double lipid layer) wherein it forms selective flow channels for $Ca^{2+}$, thereby causing a structural change in the plasmatic membrane, with formation of specific channels altering $Ca^{2+}$ permeability. The ionic channels canal activity would therefore be at the bottom of Aβ neurotoxic effect.

The effects of Aβ can thus be summarized:
alteration of neurite growth,
increase in neurons vulnerability to excitotoxicity,
destabilization of the neuronal calcium homeostasis,
toxicity consequent to aggregation,
formation of pores for $Ca^{2+}$ transport in the membrane,
promotion of the release of pro-inflammatory cytokines.

At present, no pharmacological therapies against AD exist. The only marketed medicament bearing said indication is Tacrine (INN), an acetylcholinesterase inhibitor, whose pharmacological activity is based on the block of the catabolism of the neurotransmitter acetylcholine.

The current therapeutical approaches based on β peptide turn to different strategies:
inhibition of the enzymes involved in the amyloidogenic pathway (β-secretase),
products which either block Aβ-induced neurotoxicity or stabilize neuronal cells preventing their sensitization to intracellular calcium,
Aβ ionic channels blockers or modifiers,
compounds inhibiting Aβ aggregation, even modifying the hydrophobic domain which apparently causes the amyloidogenic properties.

Atherosclerosis

Atherosclerosis is an extremely complex and variable pathology wherein some components of different nature deposit in plaques adhering to the intima of blood vessels. Said formations cause a local damage to the vessel and an increase in the circulatory resistances with a consequent pressure increase, as well as a decrease in the blood afflux to organs and tissues and therefore a functional decompensation.

Histologic characterization of the atherosclerotic plaques has not yet completely been defined: the parameters responsible for the evolution of the plaque, the mechanisms of formation and the evolution stages are still partly not clear and vary depending on determinant factors such as age, sex, diet and environment. The study of morphology and composition of complex atheromatous plaques, extracted from patients subjected to peripheral surgery, showed a remarkable heterogenicity in the chemical/biological composition of the aggregates: some formations mainly consist of lipoproteins and lipids, others of inflammation cells, others of fibrous capsules, others, most complex, of neo-formed vases.

On the other hand, the early formation stages of the atheromratous plaques have apparently some common characteristics: in particular, the presence of lipoproteins of the LDL group (Hoff HF et al. J. Lipid Res 34: 789–798 (1993); Srinivasan SR et al. Atherosclerosis 38: 137–147 (1981); Piotrowski JJ Life Sci. 58: 735–740 (1996)) seems to represent a common structural characteristic of atheromatous plaques in the early stage of deposition.

Westermark and colleagues (Am. J. Pathol. 147: 1186–1192 (1995) evidenced that amyloid deposits in aorta intima are very common in combination with atherosclerotic pathologies and aging. These researchers purified a fibrillar protein present in the extracellular deposits from patients with atherosclerosis: said protein is the N-terminal fragment 69 amino acids long of apolipoprotein A1.

At present, no effective pharmacological therapies for the treatment of the early phases of the formation of atheromatous plaques exist. Whereas surgery is the choice strategy when complex, evolved plaques are present, the patients known to be disposed to atherosclerosis cannot receive suitable preventive therapies.

Amyloidosis

Monoclonal gammapathies or plasma-cell dyscrasias are a group of clinically and biochemically different. diseases characterized by the abnormal proliferation of a cell clone normally involved in immunoglobulins synthesis.

The immunochemical characteristic of these diseases is the presence of structurally and electrophoretically homogeneous (monoclonal) immunoglobulins or of polypeptidic subunits thereof in the patient's serum or urines.

Some of these conditions are asymptomatic and apparently stable, others, such as multiple myeloma and amyloidosis, are progressive and fatal.

The etiology of monoclonal gammapathies is unknown.

Amyloidosis consists of a group of biochemically and clinically heterogeneous conditions, which are usually characterized by the deposition of proteins in fibrillar form in the tissues. Such an accumulation causes functional damage to the involved organs with an often fatal outcome.

More particularly, AL amyloidosis is due to the deposition of fibrils formed by fragments of immunoglobulin light chains. This amyloidosis is distinguished in primary amyloidosis, if the plasma-cell clone is not very large and amyloidosis associated with multiple myeloma.

AL amyloidosis is one of the most serious plasma-cell dyscrasias for which no effective treatments exist. The progress of the disease is quick and fatal, with a mean survival of only 12 months.

Prions Diseases

The term prion was brought in to define a class of particles responsible for the transmission of some neurodegenerative diseases such as Creutzfeld-Jakob disease; kuru, Gerstmann-Straussler-Scheinker (GSS) syndrome, familial fatal insomnia (FFI), bovine spongiform encephalopathy (BSE).

This type of pathologies is characterized by the accumulation in brain of a protease-resistant protein (PrPres), deriving from a protease-sensitive protein (PrPsen) of 33–35 kDa. The amino acid sequence of the two proteins is the same and they differ in the conformation. The clinical signs of the diseases coincide with the structural modification from PrPsen to PrPres, with accumulation of the latter in fibrillar structures. The histopathological characteristic of the nervous tissue from patients with prion diseases is, in fact, the presence of crystalline aggregates with a spherical structure localized at the post-synaptic evaginations. In crude brain extracts from infected rodents, fibrillar structures with a well defined morphology have been identified: two types of fibrils exist, formed by two or four helical sub-filaments; the rotation progress of the sub-filaments as well as the space among them are regular. This characteristic microscopical structure allows to distinguish between the aggregates present in prions diseases and those characterizing other diseases with plaque accumulations, such as Alzheimer's disease. Prions are highly resistant to protease action and they are usually inactivated by chemical and physical means.

Some monoclonal antibodies are capable of catalysing chemical reactions involving components recognizable by the antibody itself. Catalytic monoclonal antibodies are named abzymes and are usually prepared by using as antigen the stable analogue of the transition state of the reaction to be catalysed by the abzyme itself.

For the preparation of abzymes with protease activity, the analogue of the transition state of the peptide bond between two selected amino acids is usually employed, i.e. a dipeptide analogue; on the other hand, an abzyme with a specific protease activity is obtained this way, and any proteins containing said dipeptide in its own sequence can be the target of the abzyme. To increase the antibody specificity, attempts to use immunogens in which no more than 8 amino acids linked to the dipeptide analogue are present have been made. Also in this case, however, the resulting specificity and selectivity could not assure the absence of cross reactions between the abzyme and other protein molecules different from the target.

Moreover, abzymes have up to now been produced for the purpose of increasing reaction rates. On the contrary, no abzymes produced in order to exert activities absent or deficient in the organism affected with one of the above described pathologies are known.

Abstract of the Invention

It has now surprisingly been found that catalytic monoclonal antibodies (in the following abzymes) with protease activity can be prepared without using the stable analogue of the transition state. Most unexpectedly, using as immunogen the protein agent responsible for or involved in pathologies characterized by plaques or aggregates with a protein component, abzymes with protease activity extremely selective towards the protein component of the plaque or of the aggregate characteristic of the concerned pathology can be obtained.

It is therefore an object of the present invention an abzyme or a fragment thereof or an engineerized fragment thereof which participates in the cleavage reaction of protein molecules whose presence, either in the free or in the aggregated form, is related to pathologies of various apparatuses and organs.

A further object of the present invention is a process for the preparation of said abzyme.

Still a further object of the present invention are pharmaceutical compositions containing said abzyme or a mixture of abzymes and medicaments useful for the treatment or the prevention of pathologies related to proteins in the free or aggregated form against various apparatuses and organs.

These and other objects of the invention, in the various embodiments there of, will be described in the following in greater detail also by means of examples.

Detailed Disclosure of the Invention.

According to the present invention, the abzyme has protease activity against protein molecules whose presence, either in the free or in the aggregated form, is related to pathologies of various apparatuses and organs.

As a rule, according to the present invention, the abzyme is obtained using directly its protein target as immunogen agent, with no need for a synthetic derivative of the analogue of the transition state.

The process comprises:
a) immunizing an animal with the target of the abzyme
b) obtaining the hybridoma
c) selecting the hybridomas for their catalytic activity.

The process for the preparation of the abzyme is effected with conventional techniques for the preparation of monoclonal antibodies, such as in vivo immunization, in vitro immunization and phage display.

The resulting antibody can be integer, or only the part of the molecule maintaining the catalytic activity can be isolated and used. The present invention also comprises any modification deriving from engineerization processes, such as single chain variable fragment (ScFv), or from modification processes, such as fragment antigen binding (Fab) and equivalent analogues.

In a first preferred embodiment, the abzyme is direct against $A\beta_{1\text{-}42}$.

Said abzyme selectively recognizes the $A\beta_{1\text{-}42}$ assembled in senile plaques and is capable of exerting a peptidase catalytic activity specifically against it, cleaving it into smaller fragments, which can easily be metabolized and which show no aggregating activities. Such an approach would allow for the treatment of patients both in early and late stages of the disease, although in the latter condition the neurodegenerative process is already advanced and irreversible.

It is essential for the abzyme against $A\beta_{1\text{-}42}$ that the immunogen, i.e. the fragment itself of the β amyloid 1–42 fragment be in a β-sheet conformation.

The intended use of the $A\beta_{1\text{-}42}$ fragment as an immunogen agent is due to the fact that the core of the amyloid insoluble extracellular deposits consists mainly of $A\beta_{1\text{-}42}$. Furthermore, $A\beta_{1\text{-}42}$ is, among the various fragments, the one with the highest amyloidogenic properties, i.e. it is highly capable of associating into more and more complex aggregates and assembling in fibres. $A\beta_{1\text{-}42}$ is, in fact, more hydrophobic than other fragments and its aggregation rate is higher.

The secondary structure of the peptide has been found to be of extreme importance for its neurotoxic activity (Simmons, Mol. Pharmacol. 45:373–379 (1994), and the 1–42 fragment exerts its action only after reaching the planar β-sheet conformation. Considering that $A\beta_{1\text{-}42}$ has a planar β-sheet conformation also in the amyloid plaques, it is necessary to use the peptide in its secondary structure as the immunogen. Commercial $A\beta_{1-42}$ (fresh) has a random coil structure; the β-sheet conformation can be obtained by incubation of the fresh $A\beta_{1-42}$ in aqueous solution for some days (aging): this treatment determines a conformational transition from random coil to β-sheet (Simmons, 1994), obtaining aged The immunogen can optionally be linked to a protein carrier, when the immunogen itself does not have sufficient size to evoke a suitable immune response or if this is considered useful in the practice of the present invention.

In a second preferred embodiment, the abzyme is directed against monoclonal immunoglobulins, or their polypeptidic subunits typical of monoclonal gammapathies, for example multiple myeloma and amyloidosis.

In a third preferred embodiment, the abzyme is directed against apolipoproteins, for example apo A and/or apo B, responsible for atherosclerosis.

In a fourth preferred embodiment, the abzyme is directed against prions.

A further aspect of the present invention relates to the method for the selection of hybridomas. Conventionally, hybridomas are selected with affinity techniques. Said techniques, however, do not select the abzymes on the basis of the catalytic activity so that the selected abzymes sometimes are not those having the best activity. According to the present invention, the selection is carried out contacting the hybridomas with a staining reactive which reveals that the concerned catalytic reaction has taken place. The detection of the reacted species can be carried out with conventional procedures, for example calorimetric or spectrophotometric techniques.

The following example further illustrates the invention.

EXAMPLE

Abzyme Against $A\beta_{1-42}$.

$A\beta_{1-42}$ synthetic fragment in aqueous solution, prepared according to a process illustrated below, has been used as antigen to inject to 8 weeks old Balb/c mice. Plaques from AD patients can also be used.

After carrying out the immunization, according to conventional schemes, the splenocytes from the immunized animal are fused with mouse myeloma cells, to produce hybridomas.

The selection of the hybridomas resulting from the fusion is effected according to a spectrophotometric procedure described in the following.

The Congo red dye (CR) selectively binds to β-amyloid when this is in the planar β-sheet configuration; such a structural conformation is related to the aggregation state of the peptide itself in the amyloid plaques.

When CR is added to a solution containing Aβ aggregate (aged), the dye is retained by the aggregates and, once the sample is centrifuged, it remains trapped in the pellet, with a consequent decrease in its concentration in the supernatant. The absorption difference at a wavelength of 485 nm (absorbance peak of CR) indicates the presence of the soluble peptide in the supernatant and it is therefore an index of the protease activity and of the presence of the desired abzyme.

A 100 $\mu$M solution of CR is prepared.

The aged 25 $\mu$M Aβ in PBS is prepared.

100 $\mu$l of aged Aβ are dispensed in test-tubes.

100 $\mu$l of each sample are taken from each well containing the hybridomas and dispensed in the corresponding test-tube, which is stirred and incubated at 37° C. for 1 hour. The reaction is quenched in ice.

The test-tubes are kept in ice and added with 100 $\mu$l of cold CR, then stirred, incubated in ice for 1 hour, then centrifuged at 14,000 g for 5 minutes.

In Vitro Tests

The 25 $\mu$M aged Aβ in PBS was incubated with the supernatant in the clone of selected hybridomas. After centrifugation at 14,000 g, the precipitate was resuspended.

The test-tube containing the resuspended precipitate was added drop by drop with a 1% solution of Congo red in distilled water.

After one hour incubation in ice, a plating was carried out on a slide which was observed under the optical microscope.

What is claimed is:

1. An abzyme having protease activity toward aggregate beta amyloid 1–42 protein ($A\beta_{1-42}$) in a β sheet conformation obtained by immunization with beta amyloid 1–42 protein aggregated in a beta-sheet conformation.

2. An immunogenic composition comprising $A\beta_{1-42}$ in a beta-sheet confirmation and a carrier.

3. A composition of claim 2 wherein said carrier is a protein carrier.

4. An abzyme of claim 1 wherein said beta amyloid 1–42 protein is a synthetic protein.

5. A hybridoma which produces an abyzme of claim 1.

6. A process of preparing an abzyme of claim 1 comprising the following:

a) immunizing an animal with a composition of claim 2, and b) isolating said abzyme from said animal.

7. A process of preparing a hybridoma which produces an abzyme of claim 1 comprising the following:

a) immunizing an animal with a composition of claim 2, b) preparing a hybridoma from splenocytes of said animal, and c) selecting at least one hybridoma which produces said abzymes.

8. A method of producing an abzyme having protease activity toward aggregate beta amyloid 1–42 protein ($A\beta_{1-42}$) comprising culturing a hybridoma of claim 5 and isolating said abzyme.

9. A method of preparing a medicament comprising combining a carrier and an abzyme of claim 1.

10. A composition comprising an abzyme of claim 1 and a carrier.

11. A method of disrupting amyloid containing plaques comprising contacting a composition of claim 10 with said amyloid containing plaques under conditions such that said protease activity disrupts said amyloid containing plaques.

* * * * *